(12) United States Patent
Sundman et al.

(10) Patent No.: US 7,068,379 B2
(45) Date of Patent: Jun. 27, 2006

(54) COMPACT OPTICAL CONTOUR DIGITIZER

(75) Inventors: Arjen Sundman, Santa Cruz, CA (US); Jeff Davis, Half Moon Bay, CA (US)

(73) Assignee: Amfit, Inc., Vancouver, WA (US)

( * ) Notice: Subject to any disclaimer, the term of this patent is extended or adjusted under 35 U.S.C. 154(b) by 187 days.

(21) Appl. No.: 10/407,925

(22) Filed: Apr. 4, 2003

(65) Prior Publication Data

US 2003/0212506 A1    Nov. 13, 2003

Related U.S. Application Data

(60) Provisional application No. 60/369,895, filed on Apr. 4, 2002, provisional application No. 60/387,938, filed on Jun. 12, 2002.

(51) Int. Cl.
*G01B 11/30* (2006.01)
*G01B 3/22* (2006.01)
*G06K 9/00* (2006.01)

(52) U.S. Cl. .................. 356/601; 382/100; 702/167
(58) Field of Classification Search ............... 356/601, 356/605, 608, 611, 613; 250/559.06, 559.07, 250/559.08, 559.19, 559.22, 559.24, 559.26; 600/592; 33/3 R, 4–6, 511–512, 515; 382/264, 382/266, 312, 100, 154, 318, 123, 203, 260, 382/263; 348/77

See application file for complete search history.

(56) References Cited

U.S. PATENT DOCUMENTS

| | | | | |
|---|---|---|---|---|
| 2,325,490 | A | * | 7/1943 | Elftman .................... 353/80 |
| 4,238,147 | A | | 12/1980 | Stern ........................ 354/77 |
| 4,286,852 | A | | 9/1981 | Stern et al. ................. 354/77 |
| 4,508,452 | A | | 4/1985 | DiMatteo et al. ........... 356/375 |
| 4,705,401 | A | | 11/1987 | Addleman et al. .......... 356/376 |
| 4,737,032 | A | | 4/1988 | Addleman et al. .......... 356/376 |
| 4,846,577 | A | | 7/1989 | Grindon ..................... 356/376 |
| 5,025,476 | A | * | 6/1991 | Gould et al. ............... 382/115 |
| 5,118,192 | A | | 6/1992 | Chen et al. ................ 356/376 |
| 5,371,375 | A | | 12/1994 | Stern et al. ................ 250/561 |
| 5,753,931 | A | * | 5/1998 | Borchers et al. ....... 250/559.22 |
| 5,815,275 | A | | 9/1998 | Svetkoff et al. ............ 356/376 |
| 5,870,220 | A | | 2/1999 | Migdal et al. .............. 359/216 |
| 6,205,230 | B1 | * | 3/2001 | Sundman et al. ........... 382/100 |
| 6,289,107 | B1 | * | 9/2001 | Borchers et al. ........... 382/100 |

* cited by examiner

*Primary Examiner*—Gregory J. Toatley, Jr.
*Assistant Examiner*—Roy M. Punnoose
(74) *Attorney, Agent, or Firm*—Ohlandt, Greeley, Ruggiero & Perle, L.L.P.

(57) ABSTRACT

An optical contour digitizer including a radiation source for emitting radiation therefrom, a first mirror for folding the radiation emitted from the radiation source towards an object being measured, a second mirror for folding a reflection of the radiation from the object being measured and a sensor for sensing the reflected radiation folded by the second mirror, and a method of using the same.

27 Claims, 5 Drawing Sheets

COMPACT OPTICAL CONTOUR DIGITIZER

CROSS-REFERENCED APPLICATIONS

This application claims priority to U.S. Provisional Patent Application Nos. 60/369,895, filed on Apr. 4, 2002, and 60/387,938, filed on Jun. 12, 2002.

BACKGROUND OF THE INVENTION

Optical digitization of a three dimensional (3-D) contour using a camera, structured light, and triangulation is known. Optical digitization includes using a structured light or radiation source such as, for example, a laser line projected at a known incident angle onto an object to be measured. The camera is located with the laser line in the camera's view.

Digitization systems of this type are typically calibrated to relate observed line location with contour data. The calibration can be performed by placing an object in the field of view in front of the laser line and camera and moving either the object or the camera/laser line assembly. A series of images are recorded with the relationship between the camera/laser line and the object changing a known amount between the recording of each image. The recorded image data is compared with the known geometry of the object in the field of view to determine and assign geometry values to the laser line's observed location in the camera's image data. In this fashion, the system learns how to derive geometric data from the laser line's location in the camera image. That is, the digitization system is calibrated.

There are a number of variations of the above-discussed concept. For example, one variation uses a light source of a different structure such as a matrix of lines, a grid pattern, dots, etc. The digitization system may use a polar axis rather than a linear axis for the transport of the object being measured through the field of view of the camera and the structured light source.

Systems using the basic optical digitization discussed above are known. However, heretofore such systems have been large and expensive to build. This and other disadvantages limit the application of the laser scanning technology to applications where expense and size are not relatively important factors such as applications like high end medical applications and service bureaus. For example, a 3-D digitization system using aspects of the basic scanning technique discussed above, i.e., a light source and a camera sensor, is disclosed in U.S. Pat. No. 4,705,401 to Addleman et al.

Other technologies may be used to measure the geometry of the undersurface of the object to be measured, such as a foot. These technologies include (1) contact digitizing wherein gauge pins spaced at known intervals are urged upward beneath the foot and sample the contour periodically, and (2) optical triangulation where radiation of a known characteristic is projected against the subject foot such that the resulting shape of the radiation as it contacts the foot is observed by a sensor, typically a camera. A processor is used to evaluate the observed image to determine the contour data of the object (e.g., the foot) being measured.

Contact digitizing is generally the preferred method of obtaining the undersurface of a foot when the merits of the resulting data are the exclusive criterion. A contact digitizer supports the foot while measuring. Supporting the foot allows a full weight bearing measurement to be made, while not allowing the foot to completely collapse against the flat, top surface of the scanner. This yields a supportive data set that captures the extension of the foot when weight is applied.

A laser scanner has a clear plate between the scanning mechanism and the subject being measure. In the instance of measuring a foot, if the foot is suspended above the glass plate (i.e., left free the air) the data produced by the scanner matches the shape of the foot. However, this technique requires that the foot be measured in an unweighted position. The contour date obtained from the foot in the unweighted position is not very desirable since the foot can expand by as much as size and one-half when weight is applied thereto in the course of walking. The contour produced by an unweighted measurement will over Support the foot and cause discomfort. Yet, if the foot is placed against the clear plate to simulate the weight bearing of the foot, the bottom of the subject foot is completely flat. This produces an uncomfortable and unnatural, distorted shape.

Laser scanners also have a number of other problems associated with placing the foot against the clear plate such as (1) fogging where, if the foot is not completely dry, a fog is produced on the glass that tends to compromise the measurement accuracy of the foot since the shape of the subject foot is at least partially obscured by the fog; and (2) surface refraction caused by a lack of contrast of the subject foot due to, for example a light skin tone of a bare foot placed against the clear glass plate that disperses the projected radiation when it contacts the foot. The projected light disperses inside the body. It then refracts back through the clear plate. This produces an ambiguous radiation observation, as the radiation is diffused.

SUMMARY OF THE INVENTION

The present invention uniquely achieves reductions in the size and cost of a scanning system. Thus, the present invention provides a feasible and practical solution allowing the use of laser scanning technology in areas where cost and size limitations have been a barrier heretofore. The present invention also addresses the contouring problems, some of which were discussed above, associated with laser scanning technology.

The present invention provides many additional advantages which shall become apparent as described below.

DETAILED DESCRIPTION OF THE DRAWINGS

DETAILED DESCRIPTION OF THE PREFERRED EMBODIMENT

Figure 1:
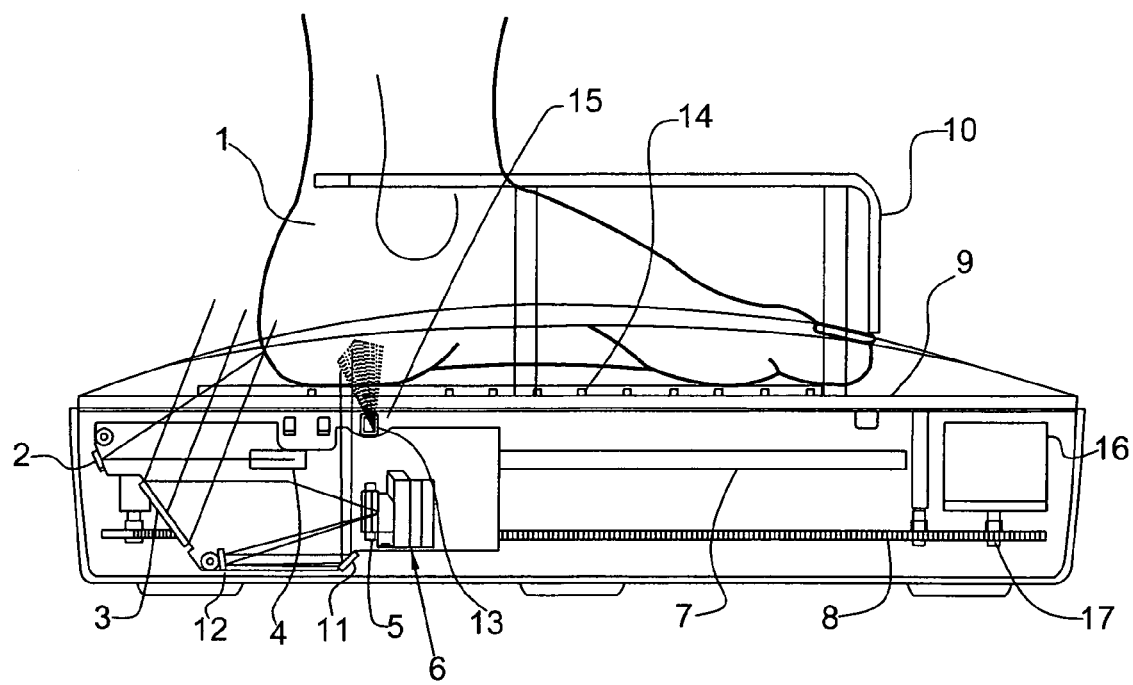
FIG. 1 is a side view of a compact optical contour digitizer in accordance with the present invention.

The present invention provides a novel architecture for structured light optical digitization. The embodiments described herein are designed to be illustrative of the architecture rather than a comprehensive, exhaustive listing of all possible implementations of the present invention.

The present invention preferably uses inexpensive components and technologies. These include, for example commodity cameras such as those used with personal computers (i.e., a digital camera). These cameras can have a fairly low resolution (640×480 pixels maximum, and even 120×170 pixels being usable). Such cameras are relatively inexpensive and designed for easy interfacing with a computer.

The camera used in an illustrative and exemplary application of the present invention can be a commercially available "webcam". The camera connects to a personal computer using a USB, serial, or other (preferably standardized) interface. The camera is preferably equipped with a pass filter. The filter can be a band-pass, high-pass, or low-pass filter to allow the passage of the desired spectrum of the radiation (e.g., light) of the structured emission source to pass through to the camera, but rejecting to a great degree other emissions that may come into the camera's view. For example, the camera can be outfitted with a filter to reject ambient light that may come into the field of view of the camera.

In one aspect hereof, a structured emission source is provided by a laser diode having a convex plastic lens at the emission end of the laser. The lens spreads the laser emission outwards in an axis to produce a line on a surface intersected by the laser emission. Laser diodes are relatively inexpensive and are also widely available.

The present invention is preferably compatible with and uses standard computing interfaces and communication protocols, thereby facilitating connection to commercially available computers and other processing peripherals using standard communication interface protocol(s). The USB interface is one such interface, as it is ubiquitous and requires little or no special skills to connect to. The ease of connection makes the present invention all the more useful. The USB interface facilitates use of an off-the-shelf, commercially available digital camera having a USB interface.

In an aspect of the present invention, an interface was designed to allow the USB connection to be used for the control of miscellaneous functions of the compact optical contour digitizer of the present invention. This aspect of the present invention contributes towards maintaining low costs and improves the practicality and reliability of the present invention.

The control electronic aspects of the present invention provide for control of motion along an axis, control of the radiation source, positioning control, and control of projection means used to illuminate the subject matter having its contour digitized. The projection means allows for direct imaging of the subject matter, as well as contour measurement. Direct imaging is desirable to derive metrics of the subject matter. In one aspect hereof, metrics are used to determine a length and a width of the foot (or any other subject matter being measured).

As discussed above, measuring an unweighted foot does not provide a complete set of data desirable for fully capturing the contour of the foot since the foot expands when weighted. Also, placing the foot on the glass plate of the scanner introduces other problems (e.g., fogging and over-flattening of the foot). Yet it is desirable to fully understand the contour of a weighted foot for the purpose of, for example, manufacturing customized orthotic supports.

It is also noted that the valid data area in the image does not include areas below the transverse column structure. If there is any refraction of the laser source light against any fogging that may occur, it is automatically ignored by the digitizing software when using the transverse column support structure.

The embodiment shown in FIG. 1 is a contour digitizer designed to measure the shape of the plantar surface of a human foot. This particular application of the present invention uses the digitizer to measure the foot for the purpose of fabricating an orthosis for the foot.

Reference to the figures reveals that a laser mirror 2 is used to fold the emission path from the emission source of laser emitter 4. This folding of the emission source reduces the overall size required, both height and length, the emission path. Image mirror 3 is used to fold the return image path of the object being measured to camera 6. The included image mirror 3 reduces the overall size required for the returned image path and the compact optical contour digitizer.

FIG. 1 demonstrates an illustrative embodiment of the present invention. A carriage assembly can be moved along an axis 7. In the illustration, the motion occurs in a left/right direction. The carriage assembly includes a support 13 that carries a camera 6, a red pass filter 5, an image mirror 3, laser emitter 4 having a line generating optic, and laser mirror 2. The carriage assembly is moved along axis 7 using a drive system. The drive system can include a motor 16, a sprocket 17, and a belt 8. Laser 4 transmits its emission against mirror 2 and through transparent plate 9 onto subject surface 1.

An image of the subject surface is transmitted through transparent plate 9 onto image mirror 3, through red pass filter 5 and viewed and captured by camera 6.

In a preferred embodiment, the apparatus of the present invention is compact to allow for improved portability, cost, packaging, and to provide a low profile unit. The low profile of the apparatus of the present invention is important as an application thereof is the measuring of the undersurface of the foot. To facilitate ease of use and accurate, reliable measurements, it is desirable to have the measurement surface as close to the floor as possible so that the foot is not necessarily lifted up high off of the ground.

According to another aspect of the present invention, the compact optical contour digitizer of the present invention uses an assembly of mirrors to fold the laser line path, as well as the image that is observed by the camera. This folded path greatly reduces the height (roughly 50% thinner) of the device of the present invention as compared to an unfolded arrangement. Reductions in the length of the compact optical contour digitizer of the present invention are also obtained due to the configuration thereof. For example, the present invention as shown in the illustrative embodiment of FIG. 1 achieves about 100 mm length reduction in length as compared to heretofore scanners.

A light shield 10 is preferably placed around the subject object as shown to reduce ambient light (and other undesired signals/emissions) from interfering with images as viewed by camera 6.

In one aspect of the present invention, a method is provided to measure and capture the contour of the foot by looking directly at the foot. This process is desirable for determining perimeter metrics of the foot. The laser scanner of the present invention is ideal for measuring 3-D contour information, however there are some constraints regarding the field of vision with respect to the main mirror 3. For instance, the scanner has a field of vision of about 45 degrees up or down from the main mirror 3. In the illustrated scanner, portions of an object may not been seen accurately. There is a tangential (parallax) error associated with the length measurement of the foot.

In a direct view, i.e., one that is perpendicular to the reference surface, a view that provides accurate perimeter measurement is possible. The direct view aspects of the present invention are obtained using a separate emission source 15, and a return mirror 11, 12 path back to the view camera.

Figure 2:
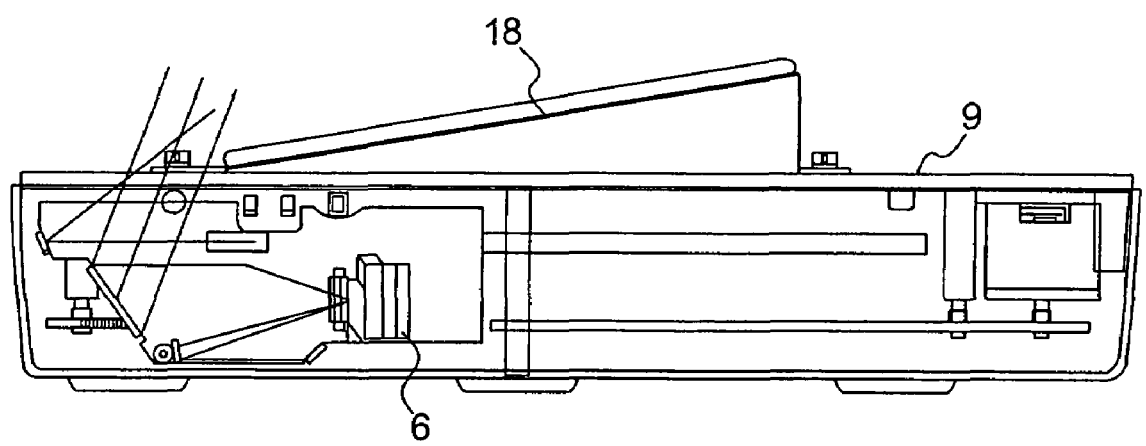
FIG. 2 is a side view of the compact optical contour digitizer of FIG. 1 having a calibration plate placed in the field of view of the camera for performing a calibration according to the present invention.

When a calibration is performed, a known geometry, for example a calibration plate 18 is placed in the field of view of camera 6. See FIG. 2 for an exemplary set-up for performing a calibration using the present invention. As shown, it is seen that the calibration set-up of FIG. 2 replaces an object of variable, unknown contour with a known calibration plate 18. The system is calibrated by obtaining contour data for the calibration plate 18 and comparing the obtained data with the known geometry values of calibration plate 18. The system is then adjusted to ensure that accurate measurements are obtained for objects to be measured by compensating for errors determined during the calibration process.

Figure 3:
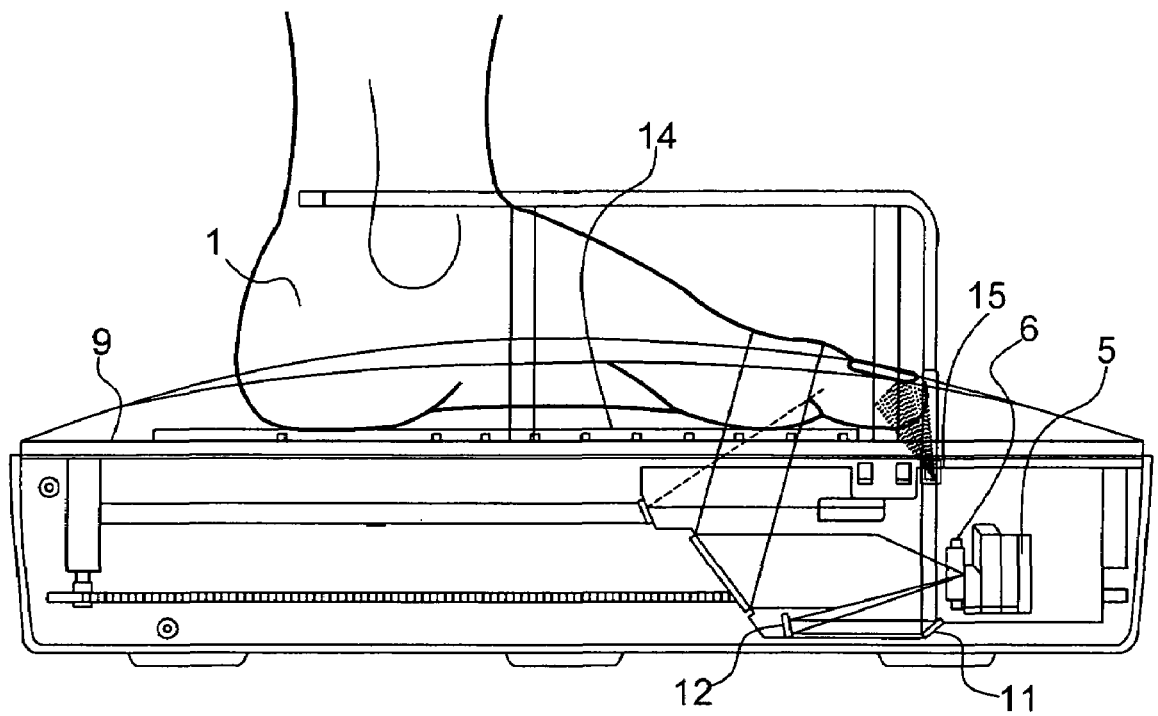
FIG. 3 is a depiction of the present invention configured for direct viewing of the subject object.
Figure 4:
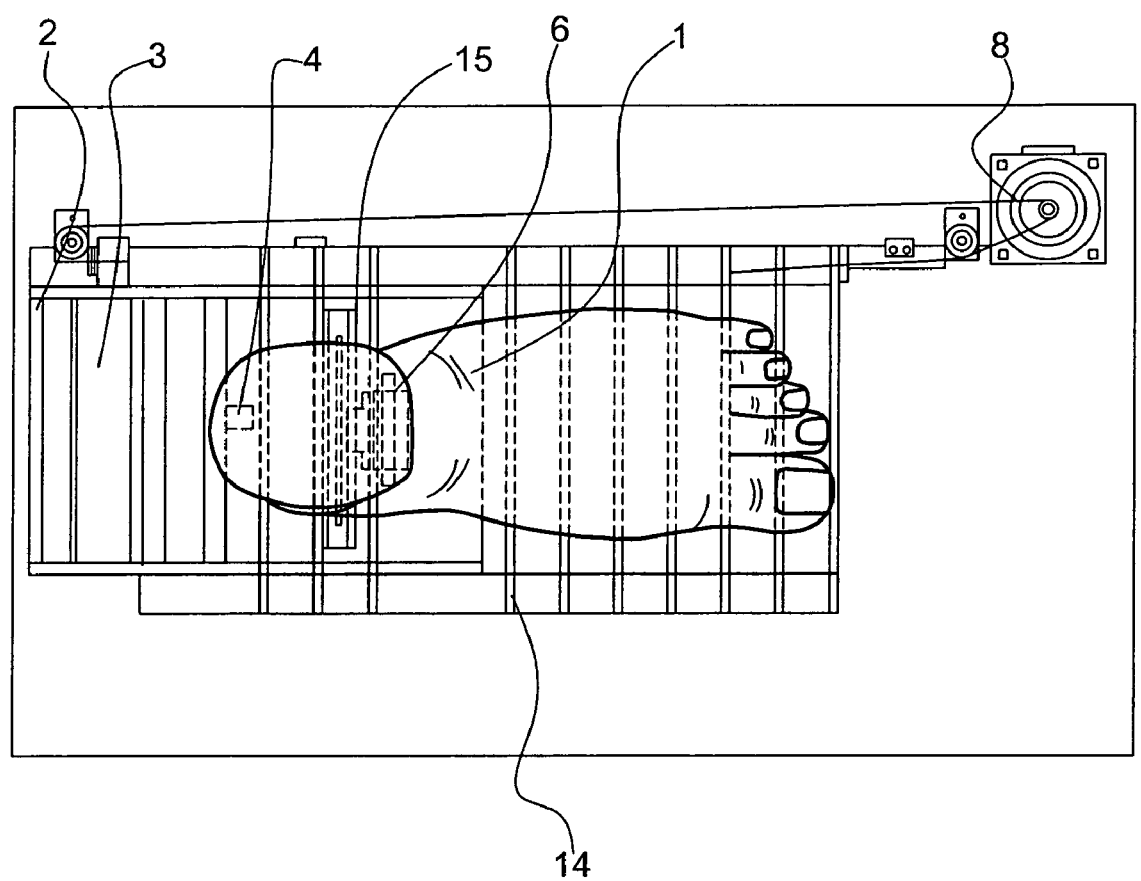
FIG. 4 is a plan view of the compact optical contour digitizer of FIG. 1.

As demonstrated in FIGS. 1, 3, and 4 there is a transverse support column spacer 14 that contacts the foot in at least a subset of the overall plantar surface of the foot. The transverse support column spacer 14 allows weight to be placed on the foot, thereby extending the length of the foot and still allowing the natural shape of the foot to be captured.

A shown, an array of ribs are placed between the subject foot 1 and the clear plate 9. The transverse support column spacer 14 is spaced above the clear plate. The reason transverse support column spacer 14 is spaced away from the clear plate is to address the problems discussed above, namely fogging and surface refraction. If the foot does not contact the clear plate, these two problems are eliminated.

The transverse support column spacer 14 ribs are about 3 mm in cross section. This allows them to be strong enough to support the foot, while minimizing any data loss associated with having the rib obscure the subject foot.

In an aspect of the invention herein, the transverse column support structure 14 is provided above and parallel to the top transparent surface 9 of the compact optical contour digitizer to support the foot 1 and allow the scanner to observe the quiescent state of the foot's surface while allowing for the application of weight to the foot. This allows for the capture of a substantial subset of the undersurface of the foot 1 in an expanded state without the flattening normally caused by applying weight to the foot placed directly on the glass top plate of the scanner.

In an aspect of the present invention, the compact optical contour digitizer of the present invention overcomes the "fog" problem caused by moisture on the foot by spacing the foot 1 away from the top transparent surface 9 of the scanner thereof. The resulting air gap minimizes any condensation on the transparent surface. The spacer is preferably the transverse column support structure used to support the foot 1. The spacer prevents or minimizes any fogging of the transparent surface 9.

Direct view of the foot is achieved by radiation emitting from a second light source 15. Light from second light source 15 radiates through transparent plate 9 against subject foot 1. Light is reflected back through transverse column spacer 14, through transparent plate 9 and onto mirror 11 and mirror 12, through filter 5 and back to camera 6.

In this manner, the benefits of direct viewing can be gained by the present invention.

In FIG. 3, the scanner transport is positioned for viewing the end of the subject foot 1. Radiation emitting from second light source 15 radiates through transparent plate 9, against subject foot 1, and is then reflected back through transverse column spacer 14, through transparent plate 9, against mirror 11 and mirror 12, through filter 5 and back to camera 6. By using the second light source 15, the end of subject foot 1 may be accurately captured without accuracy compromised due to parallax errors.

In an aspect of the present invention, the direct view optical subsystem is located further down the lengthwise distance of the scanner system. This set-up reduces the overall length of the scanner. In one embodiment, this offset is approximately 80 mm. Such an arrangement directly reduces the overall length of the scanner by a similar amount, that is, by approximately 80 mm. The offset is possible in that the direct view of the foot is only essential in the forefoot. The heel of the foot is fully digitized by the laser optical system.

FIG. 4 depicts a plan view of a preferred embodiment of the compact optical contour digitizer of the present invention. Note that the transverse column spacer 14 is shown, partially obscured by subject foot 1 as indicated by the broken lines therein.

Figure 5:
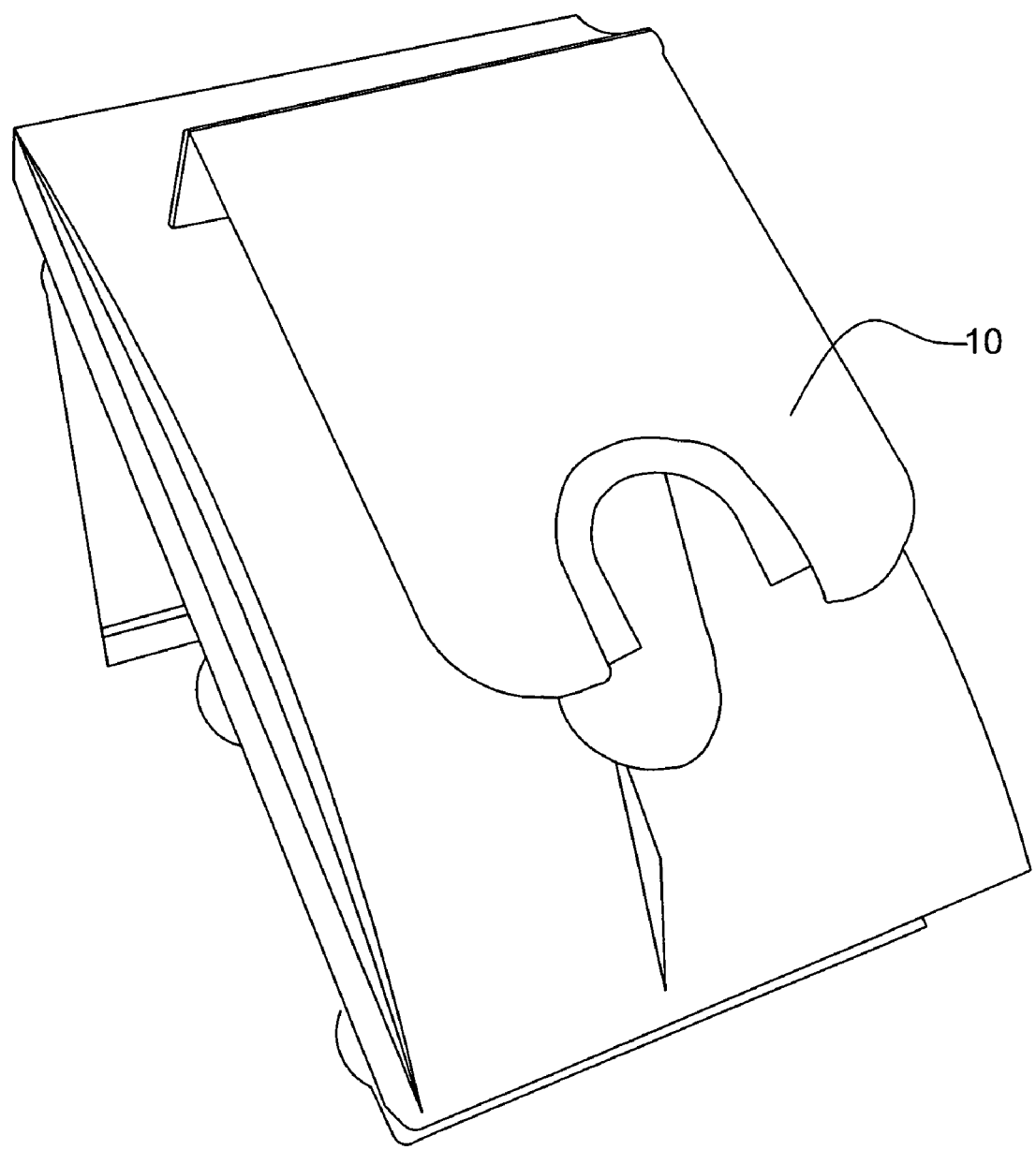
FIG. 5 is an exemplary illustration of a compact optical contour digitizer embodiment in accordance with the teachings of the present invention.

FIG. 5 shows an exemplary embodiment of the compact optical contour digitizer of the present invention, including light shield 10.

While we have shown and described several embodiments in accordance with our invention, it is to be clearly understood that the same are open to numerous changes apparent to one skilled in the art. For example, the transverse support column spacer may be configured with the support members thereof arranged in a rectangular grid, arranged diagonally with respect to the top of the transparent glass surface, etc. without departing from the scope of the present invention. Therefore, we do not wish to be limited to the details shown and described but instead incorporate all such changes and modifications that are within the scope of the claims appended hereto.

What is claimed is:

1. An optical contour digitizer comprising:
   a radiation source for emitting radiation therefrom;
   a first mirror for folding said radiation emitted from said radiation source towards an object being measured;
   a second mirror for folding a reflection of a said radiation from said object being measured;
   a sensor for sensing said reflected radiation folded by said second mirror;
   a transparent surface located above said radiation source and said sensor; and
   a transverse column spacer disposed on or above said transparent surface, wherein said transverse column spacer allows at least a portion of said reflected radiation to pass therethrough.

2. The optical contour digitizer of claim 1, wherein said object being measured is disposed on or above said transparent surface.

3. The optical contour digitizer of claim 1, wherein said transverse column spacer forms an air gap between said transparent surface and an upper support surface of said transverse column spacer.

4. The optical contour digitizer of claim 1, wherein said transverse column spacer comprises a plurality of spaced apart structures oriented transverse to said transparent surface.

5. The optical contour digitizer of claim 1, further comprising a second radiation source for directly illuminating said object being measured with radiation from said second radiation source.

6. The optical contour digitizer of claim 5, wherein said second radiation source is movable along an axis of said optical contour digitizer.

7. The optical contour digitizer of claim 5, wherein said second radiation source is disposed substantially near one end of said optical contour digitizer.

8. The optical contour digitizer of claim 5, further comprising at least one additional mirror for folding a reflection of said radiation of said second radiation source reflected from said object being measured.

9. The optical contour digitizer of claim 8, wherein said at least one additional mirror cooperates in folding said reflection of said radiation of said second radiation source toward said sensor.

10. The optical contour digitizer of claim 1, further comprising a filter disposed between said sensor and said reflected radiation folded by said second mirror.

11. The optical contour digitizer of claim 10, wherein said filter is selected from a group consisting of: a band pass, a high pass, and a low pass filter.

12. The optical contour digitizer of claim 1, wherein said radiation source is selected from a group consisting of: a light, a light emitting diode, a laser, an infrared generator, and an acoustic wave generator.

13. The optical contour digitizer of claim 1, further comprising a shield for shielding unwanted radiation from at least said second mirror.

14. The optical contour digitizer of claim 1, wherein said sensor is selected from a group consisting of: a digital camera, a photodiode, a CCD (charge-coupled device), and a computing interface.

15. The optical contour digitizer of claim 1, further comprising a transverse column spacer having a plurality of spaced apart structures.

16. The optical contour digitizer according to claim 15, wherein said optical contour digitizer comprises a transparent surface, such that said transverse column spacer is disposed between said object to be measured and said transparent surface.

17. The optical contour digitizer according to claim 16, wherein said transverse column spacer forms an air gap between said transparent surface and an upper support surface of said transverse column spacer.

18. The optical contour digitizer according to claim 16, wherein said spaced apart structures of said transverse column spacer are oriented transverse to said transparent surface.

19. The optical contour digitizer according to claim 16, wherein said spaced apart structures are disposed between said object to be measured and said transparent surface, thereby eliminating or minimizing fogging, surface refraction, and/or flattening of said foot when weight is applied thereto.

20. The optical contour digitizer according to claim 16, wherein said transverse column spacer is dispose above and parallel to said transparent surface.

21. The optical contour digitizer according to claim 15, wherein said object is a foot and wherein said transverse column spacer contacts said foot in at least a subset of the overall plantar surface of said foot.

22. The optical contour digitizer according to claim 21, wherein said transverse column spacer allows weight to be placed on said foot and still allowing the natural shape of said foot to be measured.

23. The optical contour digitizer according to claim 15, wherein said spaced apart structures are ribs.

24. The optical contour digitizer according to claim 15, wherein each said spaced apart structure has a cross section of about 3 mm.

25. An method of capturing contour data using an optical contour digitizer comprising:
   locating a transparent surface above a radiation source and a sensor of said optical contour digitizer;
   disposing a transverse column spacer disposed on or above said transparent surface, wherein said transverse column spacer allows at least a portion of radiation to pass therethrough;
   emitting said radiation from said radiation source;
   folding radiation emitted from said radiation source towards an object to be measured with a first mirror;
   folding radiation reflected from said objected to be measured by second mirror; and
   sensing said reflected radiation folded by said second mirror by a sensor.

26. The method of claim 25, wherein said transverse column spacer supports said object to be measured thereon in a spaced relation to said transparent surface.

27. The method of claim 25, further comprising directly illuminating said object to be measured with radiation from a second radiation source.

* * * * *